United States Patent
Fukuda et al.

(10) Patent No.: US 7,065,477 B2
(45) Date of Patent: Jun. 20, 2006

(54) DEVICE AND METHOD FOR GENERATING AN ARRANGEMENT OF A SET OF PARTICLES

(75) Inventors: Ikuo Fukuda, Kanagawa (JP); Shigeru Kameda, Kanagawa (JP); Shoichi Masuda, Kanagawa (JP); Ichiro Suzuki, Kanagawa (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/435,215

(22) Filed: Nov. 5, 1999

(65) Prior Publication Data
US 2002/0049572 A1    Apr. 25, 2002

(30) Foreign Application Priority Data
Mar. 19, 1999    (JP) ................... 11-074987

(51) Int. Cl.
   *G06G 7/48*    (2006.01)
   *G01N 7/48*    (2006.01)
(52) U.S. Cl. ............................. 703/6; 702/27
(58) Field of Classification Search ............. 703/6; 702/27
   See application file for complete search history.

(56) References Cited

U.S. PATENT DOCUMENTS

| | | | | |
|---|---|---|---|---|
| 5,241,470 A | * | 8/1993 | Lee et al. ................... 436/86 |
| 5,448,498 A | * | 9/1995 | Namiki et al. ............... 702/138 |
| 5,553,004 A | * | 9/1996 | Gronbech-Jensen et al. .. 702/19 |
| 5,596,511 A | * | 1/1997 | Toyoda et al. ................ 702/41 |
| 5,596,703 A | * | 1/1997 | Eick et al. ................... 345/700 |
| 5,600,571 A | * | 2/1997 | Friesner et al. .............. 702/27 |
| 5,724,252 A | * | 3/1998 | Iijima et al. .................. 702/29 |
| 6,029,114 A | * | 2/2000 | Shamovsky et al. .......... 702/22 |
| 6,188,965 B1 | * | 2/2001 | Mayo et al. .................. 702/27 |

OTHER PUBLICATIONS

Canales et al.; "Molecular dynamics simulation of Li-Mg and Li-Na alloys"; J. Non-Crystalline Solids; pp. 907-910, Oct. 1996.*

Arai et al.; "Monte Carlo study of 4th-inverse power potential using parallel computers: the role of structure factor in low wavenumber region"; J. Non-crystalline solids; pp. 879-883, Oct. 1996.*

Konishi et al.; "Determination of N-body potential for Fe-Cr alloy system and its application to defect study"; Comp. Materials Sci.; pp. 108-113, Feb. 1999.*

Mendelev; "Computer simulations of Ag-In liquid alloys structure and self-diffusion coefficient calculations"; J. Non-Crystalline Solids; pp. 560-566, Jul. 1998.*

Merkle et al.; "Hybrid genetic algorithms for minimization of a polypeptide specific energy mode"; IEEE Proc. Evol. Comp.; pp. 396-400; May 1996.*

(Continued)

*Primary Examiner*—Hugh Jones
(74) *Attorney, Agent, or Firm*—Staas & Halsey LLP

(57) ABSTRACT

A simulation device calculates an equilibrium arrangement of a set of particles by using a potential function or a force function, which describes an interaction of a particle system, and simulates the particle system by using an obtained equilibrium arrangement as an initial arrangement.

18 Claims, 13 Drawing Sheets

OTHER PUBLICATIONS

Wang et al.; "Using an annealing genetic algorithm to solve global energy minimization problem in molecular binding"; IEEE Tools with Artificial Intelligence; pp. 404-410; Nov. 1994.*

Celino et al.; "New parallel hybrid genetic algorithm based on moleculardynamics approach for energy minimization of atomistic systems"; IEEE Conf. Evol. Comp.; pp. 115-119; Apr. 1997.*

Schulze-Kremer et al.; "Parameterizing genetic algorithms for protein folding simulation"; IEEE Proc. Sys. Sciences; pp. 345-354; Jan. 1994.*

Ibayashi et al.; "Coal molecular structure construction by genetic algorithm"; IEEE Proc. Intell. & Sys.; pp. 111-115; May 1998.*

Michaelian; "A symbiotic algorithm for finding the lowest energy isomers of large clusters and molecules"; Chem. Phys. Lett.; pp. 202-208; Aug. 1998.*

Chen et al.; "Molecular binding in structure-based drug design: a case study of the population-based annealing genetic algorithms"; Art. Intell; pp. 328-335; Nov. 1998.*

"Isothermal Molecular Dynamics Calculations for Liquid Salts", L. V. Woodcock, *Chemical Physics Letters*, vol. 10, No. 3., pp. 257-261, Aug. 1, 1971.

"Methods of Generating Dense Relaxed Amorphous Polymer Samples for Use in Dynamic Simulations", McKechnie, et al., *Macromolecules*, vol. 25, No. 5, pp. 7182-7190, 1992.

"Polymorphic Transitions in Single Crystals: A New Molecular Dynamics Method", M. Parrinello, et al., *J. Application. Phys.*, vol. 52, No. 12, pp. 7182-7190, Dec. 1981.

"Crystal Structure and Pair Potentials: A Molecular-Dynamics Study", M. Parrinello, et al., *Physical Review Letters*, vol. 45, No. 14, pp. 1196-1199, Oct. 6, 1980.

* cited by examiner

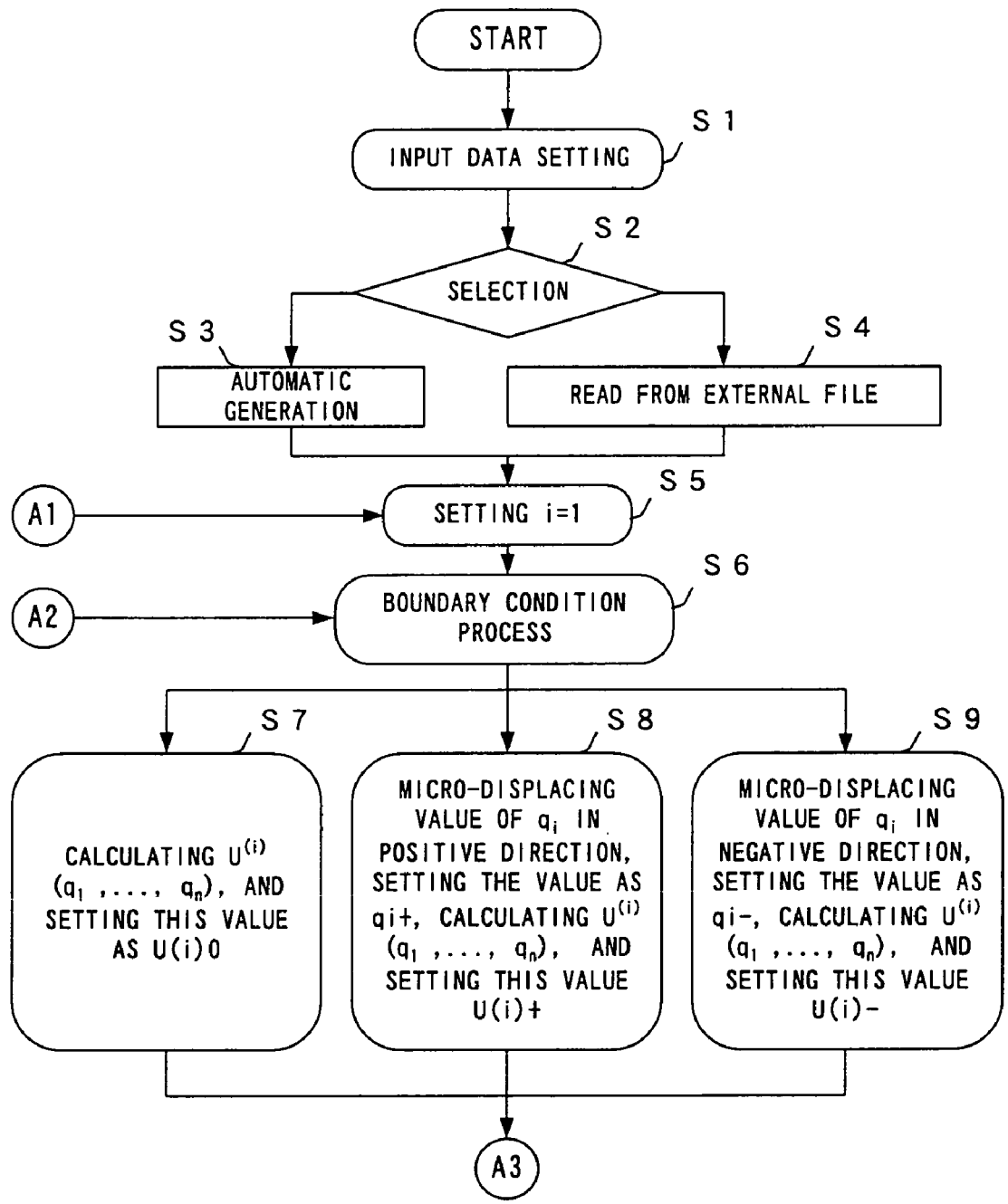
F I G. 4 A

DEVICE AND METHOD FOR GENERATING AN ARRANGEMENT OF A SET OF PARTICLES

BACKGROUND OF THE INVENTION

1. Field of the Invention

The present invention relates to a device and method for generating information representing an arrangement of a set of particles in a particle system simulation.

2. Description of the Related Art

One existing method for analyzing and predicting the nature of a material composed of an inorganic or an organic substance uses a simulation based on a Molecular Dynamics (MD) calculation. To perform this calculation, an initial arrangement of atoms or molecules, which forms the material, must be generated. In the MD calculation, attempts are made to solve a differential equation (e.g., a Newtonian equation) by using a given initial arrangement as an initial value to examine the nature of the system representing the material with a calculation result, and further, to implement the prediction of the nature.

However, experimental data on the arrangement of a system of molecules (the positional coordinates of all of the atoms forming molecules) is not obtained in many cases although the experimental data on a molecule structure considered to be a stable state of one molecule or a density of mass of the molecules at normal temperature and pressure is obtained. Accordingly, it is not known how to generate the initial arrangement of the molecules, which realizes an experimentally obtained density of mass of the molecules, when the MD calculation of a molecule system is performed.

A simple method for generating the initial arrangement of a set of particles in a unit cell is a method, which calculates the number of particles per cell from the experimental data on the density of mass of the particles, and arranges particles in the cell at random. However, if the particles are arranged completely at random, a pair of particles which have a close distance is sometimes generated. It is known that very intense force is applied between the close particles. If even one such pair of close particles exists, the velocity of the particles increase due to an interaction between them, so that the temperature of the system becomes very high locally in the neighborhood of the pair. Accordingly, a very large numerical value occurs when a differential equation is solved, which sometimes leads to a failure of a numerical value integral algorithm.

Three conventional methods to prevent such a simulation failure can be devised. Normally, these methods are combined and used in many cases.

(1) Heat Emission Method

This is a method for emitting heat of a system generated during a simulation at suitable timing. Specifically, the velocity of each particle is decreased or reduced to "0".

(2) Potential Relaxation Method

This is a method for preventing very intense force from being applied between close particles by weakening an interaction with the transformation of a potential function in a region where a distance between particles is short. With this method, the form of the potential function is continually changed during simulation, and is restored to its original function form by degrees. At this time, if all of the distances between respective particles are (equal to or) larger than a predetermined value $R_t$ as a result of the measurement of the distances between particles, the potential function is restored to the original function form. The value of $R_t$ is input as a parameter beforehand.

(3) Cell Size Change Method

This is a method for starting simulation after setting a cell whose size is larger than a size calculated from the experimental data on a density of mass of the particles. With such a cell, the probability that a pair of particles having a close distance being generated becomes small even if particles are arranged at random. At this time, if a pair of particles, whose distance is smaller than a predetermined value $R_d$, is found as a result of the measurement of the distances between particles, the particles are rearranged at random. Such a trial is iterated, and a normal simulation is started when all of the distances between particles become (equal to or) larger than $R_d$.

However, the above described conventional simulation methods have the following problems.

(1) Heat Emission Method

If a given initial arrangement happens to be an arrangement which does not cause a failure of a numerical integral algorithm, a simulation can properly work. However, there is no such guarantee. Thus, this method must be combined with any of the other methods.

Additionally, if heat emission timing is unsuitable, the simulation cannot work properly. If the timing is delayed, the numerical integral algorithm encounters a failure, or numerical errors are accumulated, which can possibly cause a failure. On the contrary, if heat is emitted too often, the velocity of respective particles slow down, so that time development of the system change becomes slow, which leads to a high calculation cost.

(2) Potential Relaxation Method

It is not easy to set parameters (such as a parameter for specifying transformation timing, and a parameter for specifying a transformed function form), and know-how is required. Although an empirically determined setting may be sometimes available, the simulation cannot properly work depending on a target system. Therefore, trial and error for setting parameters is required in many cases. Additionally, these parameters must be set for each pair of atom types so as to be effectively set. However, this setting operation becomes complex if a system is complicated.

Furthermore, it is also important that a determination condition for restoring a potential function should be suitably set. When a "go" determination for restoring a potential function to its original form is made before entering a fully equilibrium state, an extra calculation cost can possibly be incurred.

To explain this, FIG. 1A shows a simulation result which is obtained as a result of combining the heat emission and the potential relaxation methods, applied to a system of alkane molecules. In FIG. 1A, the horizontal axis represents a time (different from a calculation time) describing a physical change in a system, "U" represents the value ($gA^2 fs^{-2}$) of a potential function (internal energy), "V" represents the volume ($A^3$) of a cell, and "T" represents a temperature (K).

In this example, a "go" determination is made in the neighborhood of $0.6 \times 10^{-1}$ ps. However, since its timing is unsuitable, intense force is applied between particles after the "go" determination is made. As a result, the volume "V" of the cell is expanded. Therefore, a considerable calculation cost is required until the volume "V" approaches the value based on experimental data.

Additionally, if an interaction is not a 2-body force, the operation for transforming a potential function is difficult to be formulated.

(3) Cell Size Change Method

If a cell size is not sufficiently large, the number of times that the trial of a random arrangement for generating an initial arrangement is iterated increases, which leads to complications. However, if the cell size is too large, a lot of time is taken to restore the cell to its original size by means of experimental data. In a system where an interaction is complicated and the number of particles is large as in a system of macromolecules, the cost of the restoration is high. It may sometimes be necessary to make a calculation for several hours in a supercomputer until a density of mass of the molecules calculated from a cell size approaches experimental data.

Suppose that the simulation result shown in FIG. 1B is obtained as a result of applying the cell size change method to a system of 20 liquid crystal molecules. In FIG. 1B, the time represented by the horizontal axis and "U", "V", and "T" are the same as those shown in FIG. 1A. In this example, a calculation is required to be processed for many hours until the volume "V" converges.

As described above, it cannot be said that the method (1) through (3) are truly satisfactory methods from an ease-of-use, a general-purpose, or a calculation cost viewpoint. Therefore, an easy-to-use and highly general-purpose simulation method which never causes an algorithm failure due to a huge numerical value and which requires a low calculation cost is desired.

SUMMARY OF THE INVENTION

An object of the present invention is to provide a device and a method for generating an initial arrangement of a set of particles, which improves a particle system simulation process.

In a first aspect of the present invention, a generating device comprises a calculating unit and an outputting unit, and generates a set of particles arrangement in a particle system simulation. The calculating unit calculates an equilibrium arrangement of a set of particles in an arbitrarily dimensional space, while the outputting unit outputs an obtained equilibrium arrangement as an initial arrangement in the simulation.

In a second aspect of the present invention, a simulation device comprises a calculating unit, a simulating unit, and an outputting unit. The calculating unit calculates an equilibrium arrangement of a set of particles in an arbitrarily dimensional space. The simulating unit performs a particle system simulation by using an obtained equilibrium arrangement as an initial arrangement. The outputting unit outputs a simulation result.

BRIEF DESCRIPTION OF THE DRAWINGS

FIG. 4A is a flowchart showing the process for generating an equilibrium arrangement (No. 1);

DESCRIPTION OF THE PREFERRED EMBODIMENTS

Explained below are the details of preferred embodiments according to the present invention, with reference to the drawings.

Figure 1A:
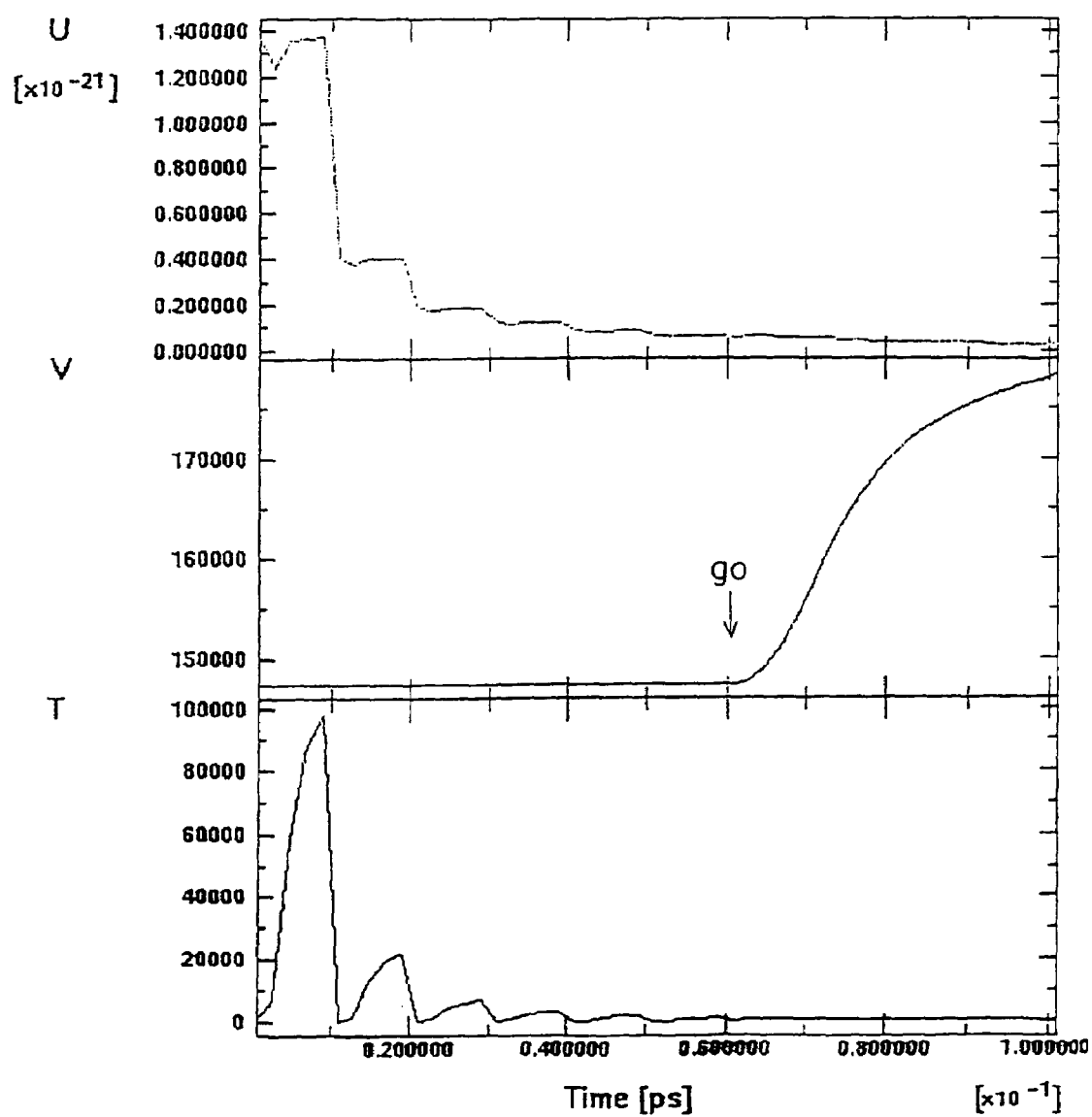
FIG. 1A shows a first conventional simulation result.
Figure 1B:
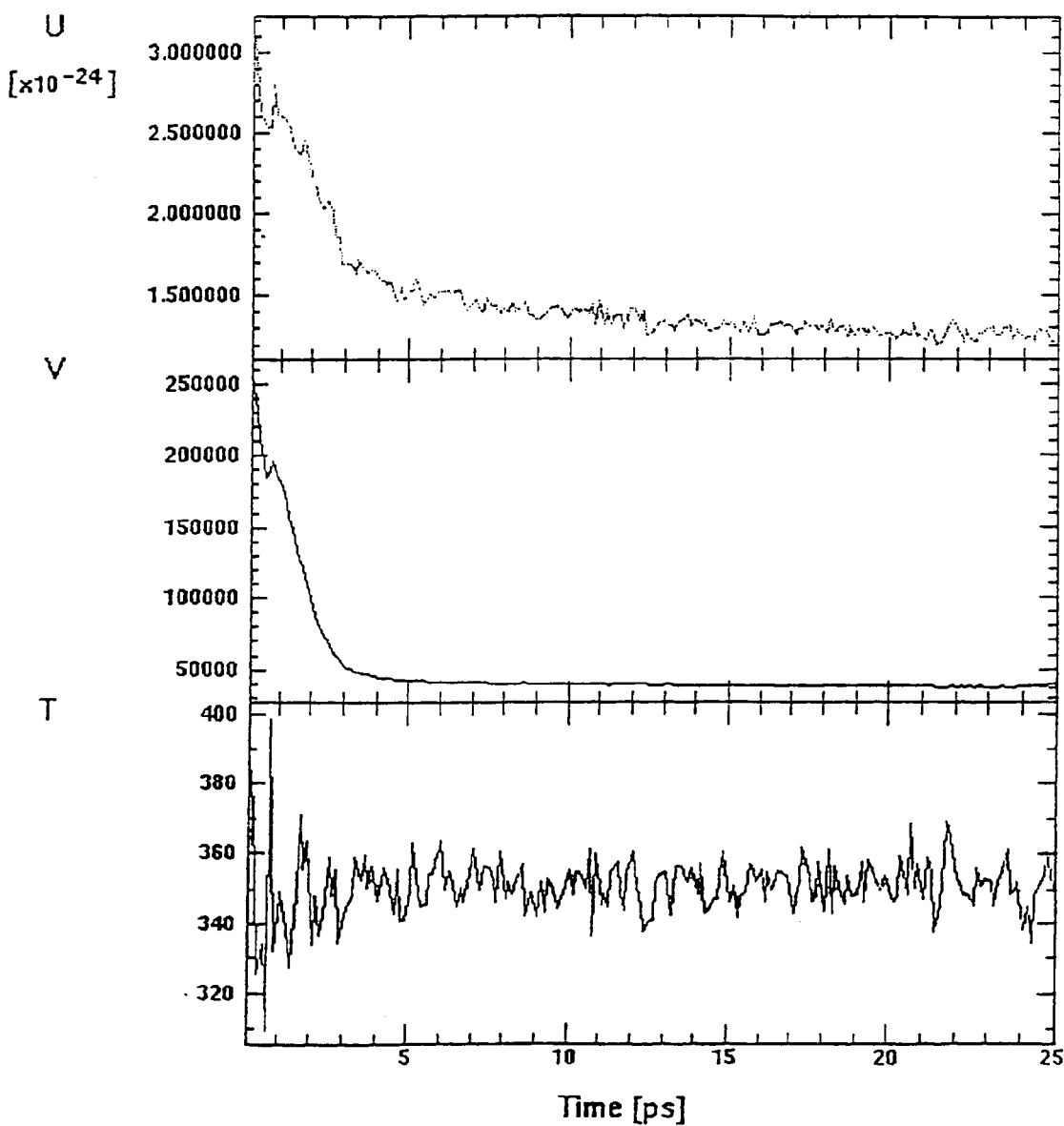
FIG. 1B shows a second conventional simulation result.
Figure 2:
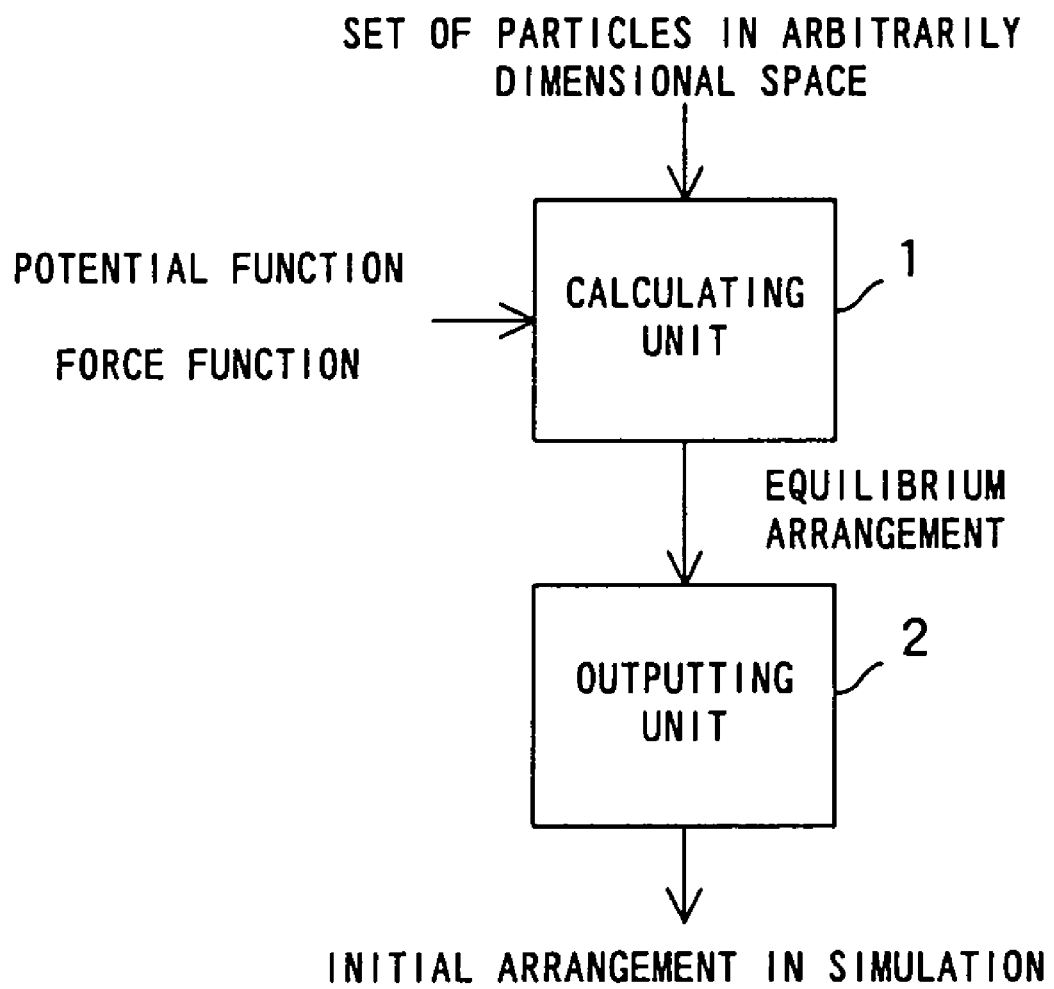
FIG. 2 shows the principle of a generating device according to the present invention.

FIG. 2 shows the principle of a generating device according to the present invention. A generating device shown in FIG. 2 comprises a calculating unit 1 and an outputting unit 2, and generates an arrangement of set of particles used in a particle system simulation. The calculating unit 1 calculates an equilibrium arrangement of the set of particles in an arbitrarily dimensional space, while the outputting unit 2 outputs the obtained equilibrium arrangement as an initial arrangement.

The equilibrium arrangement of a set of particles corresponds to an arrangement where interactions acting on respective particles are sufficiently small. This arrangement can be obtained, for example, from a potential function or a force function, which describes a particle system interaction. The calculating unit 1 calculates the equilibrium arrangement of the set of particles in a given dimensional space, while the outputting unit 2 outputs the equilibrium arrangement as the initial arrangement to a simulation program.

Since an arrangement is displaced, for example, by a predetermined amount during the generation of an equilibrium arrangement in a generating device, the displacement operation is different from conventional operations based on an acceleration and a velocity of a particle. Accordingly, there is no algorithm failure occurring due to a huge numerical value, which is caused by the acceleration and the velocity of a particle. Therefore, it is unnecessary to use the conventional heat emission method, the potential relaxation method, and the cell size change method in a simulation, thereby reducing the high calculation cost imposed by these methods. In particular, a velocity calculation required for a dynamics and a thermal calculation, a timing determination and an emission process calculation in the heat emission method, a parameter adjustment calculation in the potential relaxation method, and a cell size adjustment calculation in the cell size change method become unnecessary.

Figure 10:
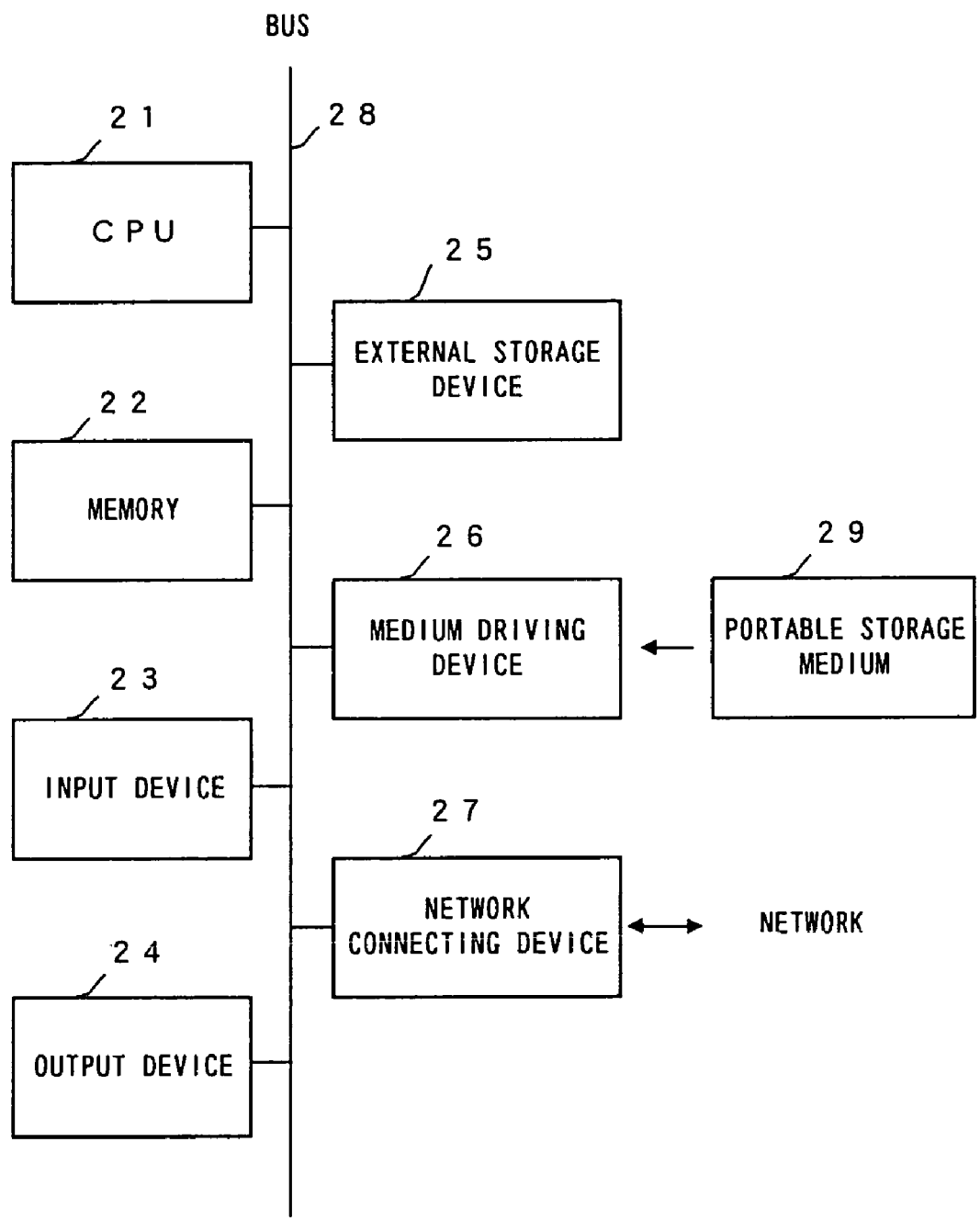
FIG. 10 is a block diagram showing the configuration of an information processing device.

For example, the calculating unit 1 and the outputting unit 2, which are shown in FIG. 2, correspond to a CPU (Central Processing Unit) 21 and a memory 22, which will be described later and are shown in FIG. 10.

Additionally, a simulation device including such a generating device comprises a simulating unit simulating a particle system by using the obtained equilibrium arrangement as the initial arrangement in addition to the calculating unit 1 and the outputting unit 2. In this case, the outputting unit 2 corresponds to an output device 24, as shown in FIG. 10, and outputs a simulation result. Furthermore, the simulating unit corresponds to the CPU 21 and the memory 22, which are shown in FIG. 10.

As described above, an aspect of the present invention is to use an equilibrium arrangement of a set of particles as an initial arrangement in a simulation. In this embodiment, given particles are not arranged at random, but an equilibrium arrangement of a set of particles is obtained by considering an interaction between particles and an obtained equilibrium arrangement is adopted as an initial arrangement in a simulation.

Consider the case where an interaction between particles is given by a potential function. In this case, an equilibrium arrangement of a set of particles composed of "N" particles is represented as a state where a system potential function "U" takes a local minimum value. Here, "U" is defined by the following equation as a continuous function which has a subset "D" of $R^n$ as a domain and takes a real number value.

$$U: R^n \supset D \to R,$$

$$q=(q_1, \ldots, q_n) \to U(q) \quad (1)$$

where "q" indicates an n-dimensional vector, and real numbers $q_1, \ldots, q_n$ indicate "n" degrees of freedom. If a space where particles are arranged is assumed to be an m-dimensional space, n=Nm. The positional vectors $r_1, \ldots, r_n$ of the respective particles are represented by the following equations.

$$r_1 = (q_1, \ldots, q_m),$$

$$r_2 = (q_{m+1}, \ldots, q_{2m}),$$

$$\ldots$$

$$r_N = (q_{(n-1)m+1}, \ldots, q_{Nm}) \quad (2)$$

Additionally, "U" can be decomposed for an arbitrary i (i=1, ..., n) as indicated by the following equations.

$$U = U^{(i)} + \overline{U}^{(i)}, \quad (3)$$

$$\overline{U}^{(i)}(q^{(i)}) - \vec{U}^{(i)}(q) = 0, \text{ for } \forall q \in D \quad (4)$$

Where $q^{(i)}$ is an n-dimensional vector defined by the following equation.

$$q^{(i)} \approx (q_1, \ldots, q_i + \Delta q_i, \ldots, q_n) \quad (5)$$

Equation (4) represents that $\overline{U}^{(i)}$ (hereinafter denoted as $U^{(i)}$ bar) remains unchanged when $q_i$ is changed by $\Delta q_i$. In other words, $U_{(i)}$ bar in equation (3) corresponds to a portion which does not depend on $q_i$ of U, while $U_{(i)}$ corresponds to a portion which depends on $q_i$ of U.

If U is represented by the sum of several terms and includes a term which does not depend on qi, U(i)=U−(U(i) bar) may be defined by setting this term to U(i) bar. In other cases, U(i)≈U, and U(i) bar≈0 may be set. For example, the potential function of a 2-body force, which is frequently used in simulations, is represented by the sum of potential functions φ between two particles by the following equation.

$$U(q) = \sum_{1 \leq i, j \leq N} \phi(\|r_i - r_j\|) \quad (6)$$

In this case, U(i) is given by the following equation.

$$U^{(i)}(q) = \sum_{j=1(j \neq i)}^{N} \phi(\|r_i - r_j\|) \quad (7)$$

Now the relationship represented by the following expression is generally satisfied between U and $U^{(i)}$.

$$U(q^{(i)}) < U(q) \Longleftrightarrow U^{(i)}(q^{(i)}) < U^{(i)}(q) \quad (8)$$

Accordingly, q may be changed to decrease $U^{(i)}$, so that U becomes small. By repeating such operations, the positions of respective particles, which correspond to the local minimum value of U, can be obtained with ease.

Figure 3:
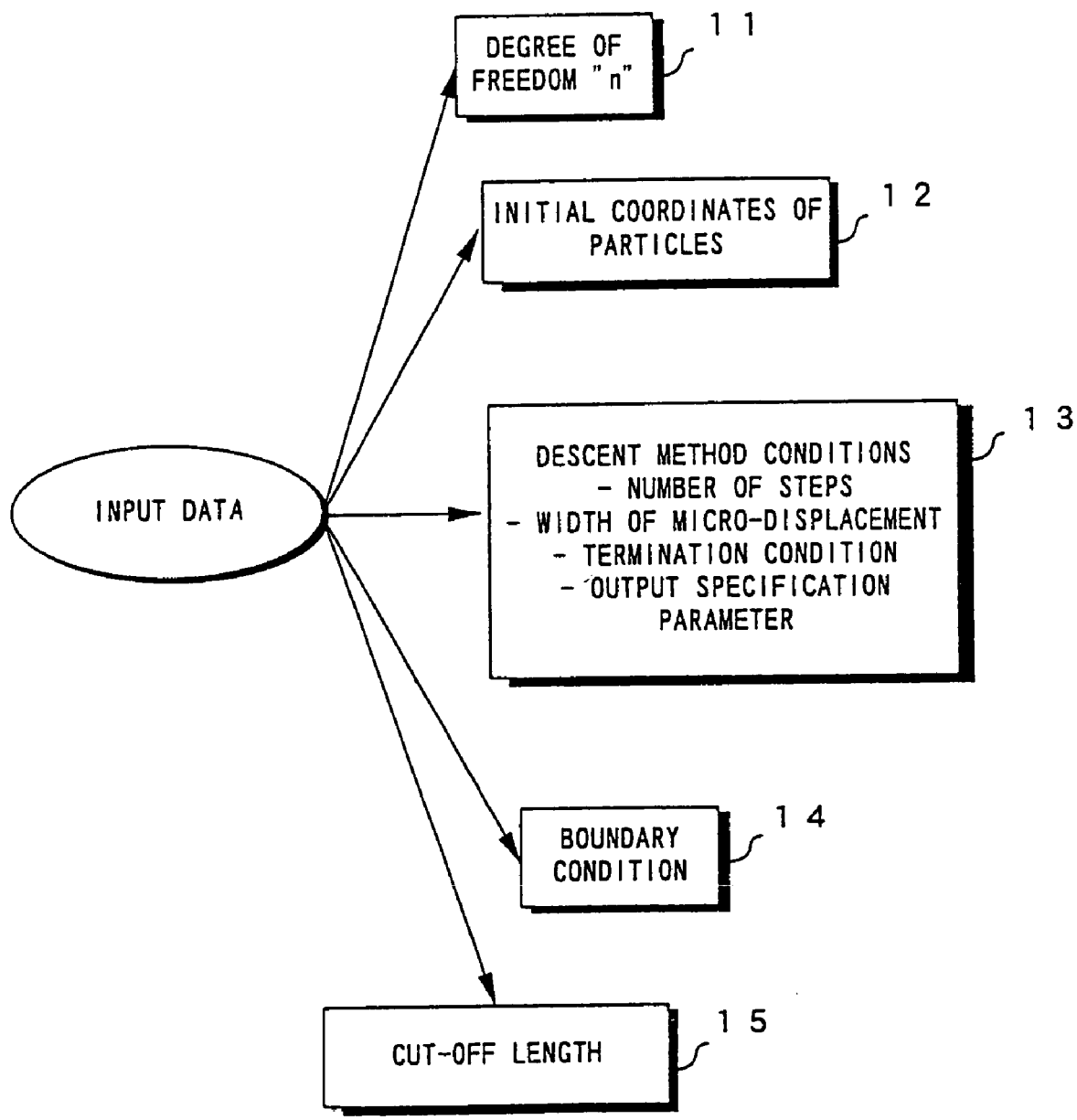
FIG. 3 shows input data.
Figure 4B:
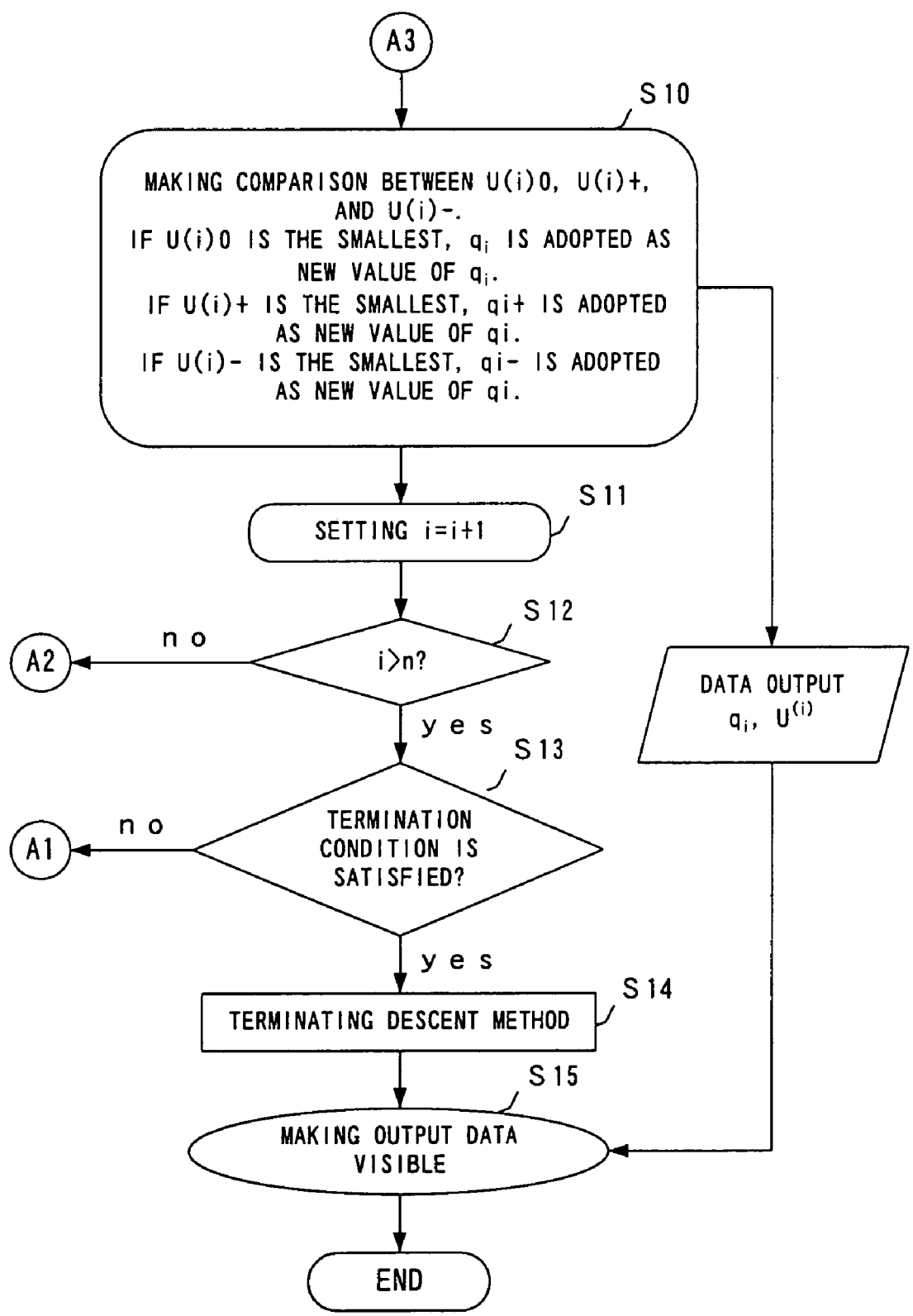
FIG. 4B is a flowchart showing the process for generating an equilibrium arrangement (No. 2)

Next, an algorithm of such an equilibrium arrangement generation process is explained by referring to FIGS. 3 through 4B.

FIG. 3 shows input data. In this input data, a degree of freedom 11 represents the number n of state variables $q_i$ describing a given problem, initial coordinates of particles 12 represent the initial positions of N particles in m-dimensional space.

Additionally, descent method conditions 13 include a number of steps, a width of a micro-displacement, a termination condition, and an output specification parameter. The number of steps represents the number of times that the descent method is iterated. The width of a micro-displacement represents an amount of displacement of the variable $q_i$. The termination condition represents a termination condition of the descent method. The output specification parameter is a parameter for specifying an output interval of data to be output.

The following are example termination conditions which are used.

(a) The iteration process is terminated when a calculation time or the number of processed steps reaches a predetermined value.

(b) The iteration process is terminated when a change in the potential U(q) becomes smaller than a predetermined determination value.

Additionally, a boundary condition 14 represents a boundary condition for the domain "D" of the potential function. For example, if a torus is specified as the boundary condition, a calculation is made by regarding the area "D" as torus (i.e., periodic boundary condition).

Furthermore, a cut-off length 15 is a parameter for simplifying an interaction. To increase an efficiency of a calculation, an interaction separated by the distance corresponding to the cut-off length 15 or more can be ignored as an optional capability.

FIGS. 4A and 4B are flowcharts showing an equilibrium arrangement generation process performed by the generating device according to the preferred embodiment. The generating device first sets input data such as shown in FIG. 3 (step S1 of FIG. 4A). At this time, the user selects an input data setting method (step S2), and either the data is automatically generated with a predetermined method (step S3) or the data is read from a predetermined external file (step S4), according to the selection of the user.

Here, n is input as the degree of freedom 11 The number of iterations, n micro-displacement sizes $\Delta 1, \Delta 2, \ldots, \Delta n$, and a convergence determination parameter $\epsilon$ (>0) are input as descent method conditions 13. Although, respectively different values are normally used as the micro-displacement sizes $\Delta 1, \Delta 2, \ldots, \Delta n$, the same value may be used as the micro-displacement sizes.

Next, the control variable "i" representing the degree of freedom is set to "1" (step S5). The boundary condition process for the potential function is performed (step S6). Then, the processes in steps S7, S8, and S9 are performed. In step S7, the value of $U^{(i)}(q_1, \ldots, q_1)$ in equation (3) is calculated, and an obtained value is set as U(i)0.

In step S8, the value of $q_i$ corresponding to an i-th degree of freedom is micro-displaced in a positive direction, and set as "qi+". Then, the value of $U(q_1, \ldots, q_n)$ is calculated by using qi+, and an obtained value is set as "U(i)+".

In step S9, the value of $q_i$ is micro-displaced in a negative direction, and set as "qi–". Then, the value of $U(q_1, \ldots, q_n)$ is calculated by using qi–, and an obtained value is set as "U(i)–". qi+ and qi– are generated by an arbitrary calculation using $\Delta i$. For the simplest calculation, qi+=$q_i+\Delta i$, qi–=$q_i-\Delta i$ may be set.

Next, the values of U(i)0, U(i)+, and U(i)– are compared (step S10 of FIG. 4B). If U(i)0 is the smallest, $q_i$ is adopted as a new value of $q_i$. In this case, the value of $q_i$ remains unchanged. If U(i)+ is the smallest, qi+ is adopted as a new value of $q_i$. If U(i)– is the smallest, qi– is adopted as a new value of $q_i$.

Next, i=i+1 is set (step S11), and i is compared with n (step S12). If i does not exceed n, the processes in and after step S6 of FIG. 4A are repeated. Such processes are repeated for i=1, 2, ..., n, so that the micro-displacements for all of the degrees of freedom are made.

If i exceeds n in step S12, it is then determined whether or not a predetermined termination condition is satisfied (step S13). If the termination condition is determined not to be satisfied, the descent method process in and after step S5 of FIG. 4A is repeated. When the termination condition is determined to be satisfied, the descent method process is terminated (step S14), $q_1, \ldots, q_n$, $U^{(1)}(q_1, \ldots, q_n), \ldots, U^{(n)}(q_1, \ldots, q_n)$, and $U(q_1, \ldots, q_n)$ at that time are output as output data (step S15). Here, the process is terminated.

The termination condition in step S13 is, for example, a condition that a suitable convergence condition for a change in the potential function is satisfied, or a condition that the descent method is terminated when the number of iterations reaches an inputted number of iterations. As the convergence condition, for example, the condition represented by the following expression using a convergence determination parameters is utilized.

$$|U^{(i)}(q_i, \ldots, q_n) - U(i)0|/|U(i)0| < \epsilon$$

$$\text{for } i=1, \ldots, n \quad (9)$$

Furthermore, in step S15, the positions of N particles are made visible on a display screen by using the obtained $q_1, \ldots, q_n$, and the equilibrium arrangement of the N particles is displayed. The data $q_1, \ldots, q_n$ representing the equilibrium arrangement is used as initial arrangement data in a MD simulation.

Here, the same $\Delta i$ is used in each iteration of the descent method. However, $\Delta i$ may be changed each time the descent method is iterated. Additionally, various conditions can be used as a convergence condition other than the condition represented by expression (9).

With such an algorithm, parameters such as the number of times that the descent method is iterated, the convergence condition, and the like can be set with ease, which eliminates the need for making a complicated parameter setting as required in the conventional potential relaxation method. Accordingly, no particular know-how is needed, so that an equilibrium arrangement can be generated with ease.

Considered next is the case where the interaction between particles is given by the force function (a continuous function) represented by the following expression.

$$F: R^n \supset D \to R^n,$$

$$q=(q_1, \ldots, q_n) \to F(q) \quad (10)$$

where F(q) represents an n-dimensional force vector. In this case, an equilibrium arrangement of N particles is given by an n-dimensional vector q by which F(q) becomes equal to "0". Accordingly, a function "U" is defined by the following equation with the use of a continuous and strictly monotone increasing function "h".

$$U(q_1, \ldots, q_n) = g(\|F(q_1, \ldots, q_n)\|) \quad (11)$$

Then, U is handled similar to the potential function U represented by equation (3), and the state where its local minimum value is realized is obtained. The positions of respective particles in the obtained state correspond to an equilibrium arrangement. Generally, the case where an interaction is given by a force function includes the case where the interaction is given by a potential function, which is considered to be applicable to many more problems.

As described above, according to this preferred embodiment, interactions (such as an N-body interaction, an interaction given by a force function,) can be handled in a general-purpose manner in addition to the 2-body interaction represented by equation (6).

Explained next is a specific example of the case where an interaction is given by a potential function. Assume that the potential function is given by the equation (6), and $\phi$ in the equation (6) is given by the following equation in a simulation of 100 argon atoms in a two-dimensional space (on a plane).

$$\phi(r) = \epsilon((\sigma/r)^{12} - (\sigma/r)^6) \quad (12)$$

Here, $\epsilon$ and $\sigma$ are positive real numbers, and are set as parameters. In this case, an equilibrium arrangement is generated with the above-described algorithm by setting m=2, N=100, and n=200.

Figure 5:
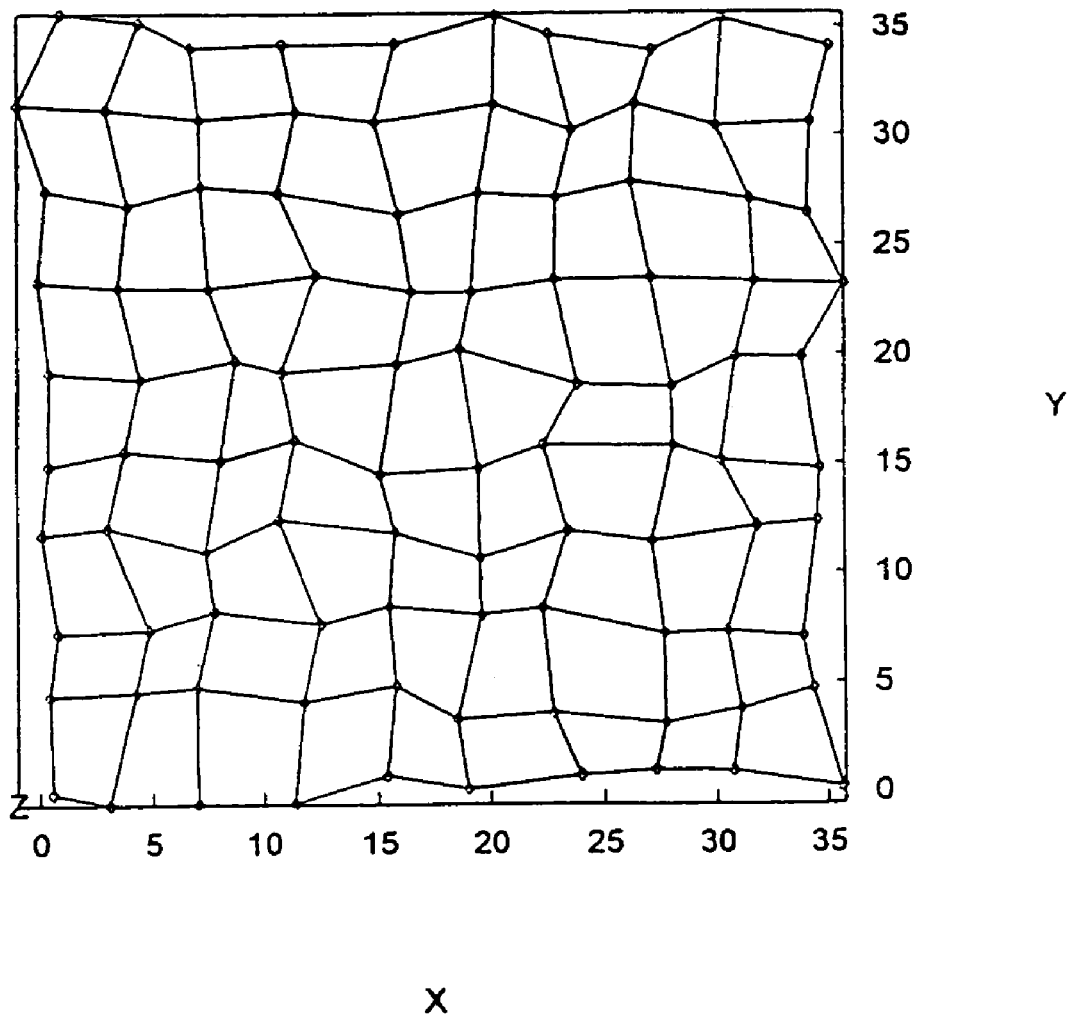
FIG. 5 shows a pseudo-random arrangement.
Figure 6:
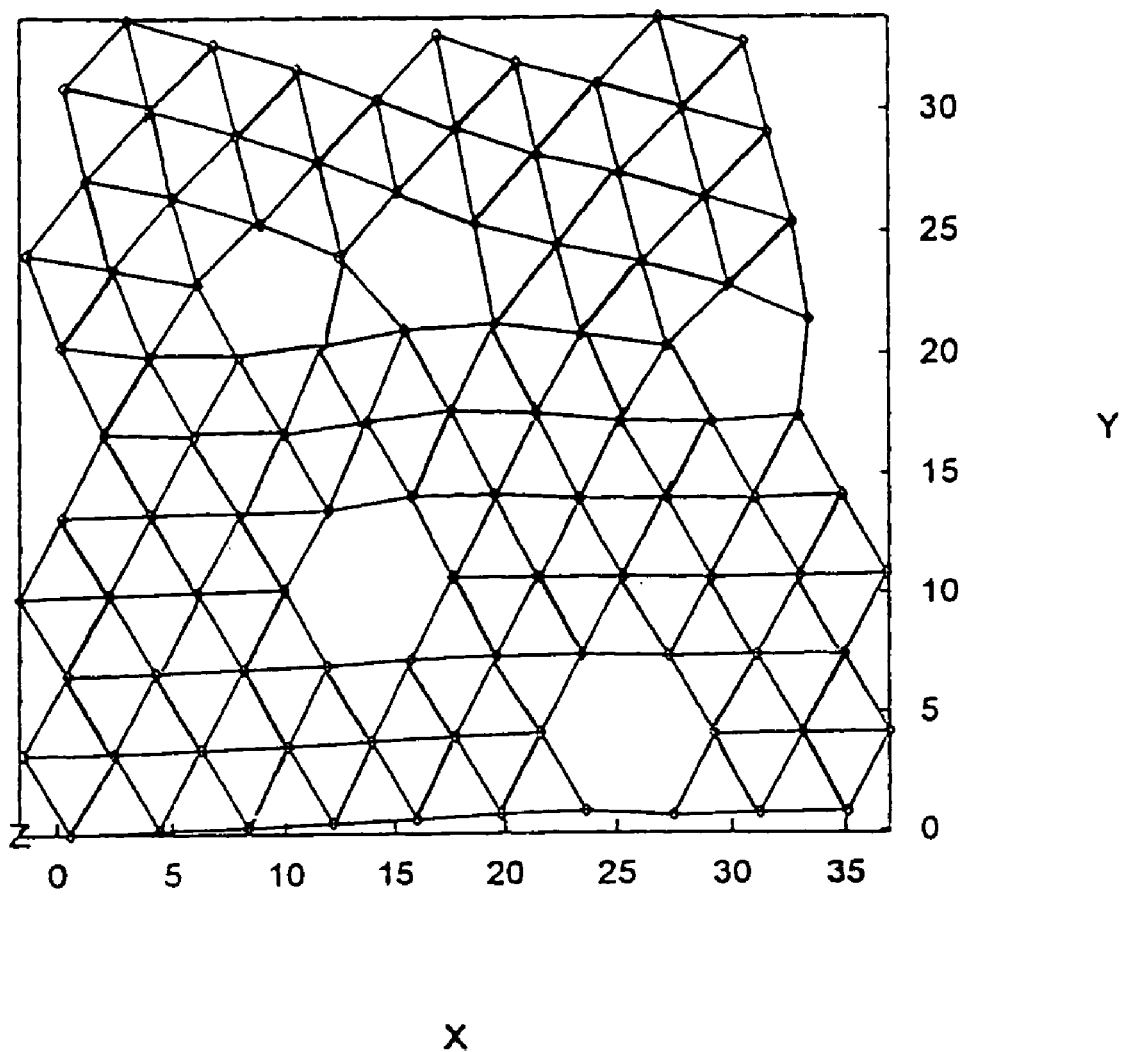
FIG. 6 shows a first equilibrium arrangement.

FIG. 5 shows a result obtained by slightly shifting 100 argon atoms from the positions of square lattices (pseudo-random) on an X-Y plane. As a result of calculating an equilibrium arrangement with the algorithm shown in FIGS. 4A and 4B starting from this arrangement, the arrangement shown in FIG. 6 is obtained. In this figure, something like a lattice defect is observed in some places. However, an arrangement analogous to an experimentally acquired FCC (Face Centered Cubic) structure is obtained.

Figure 7:
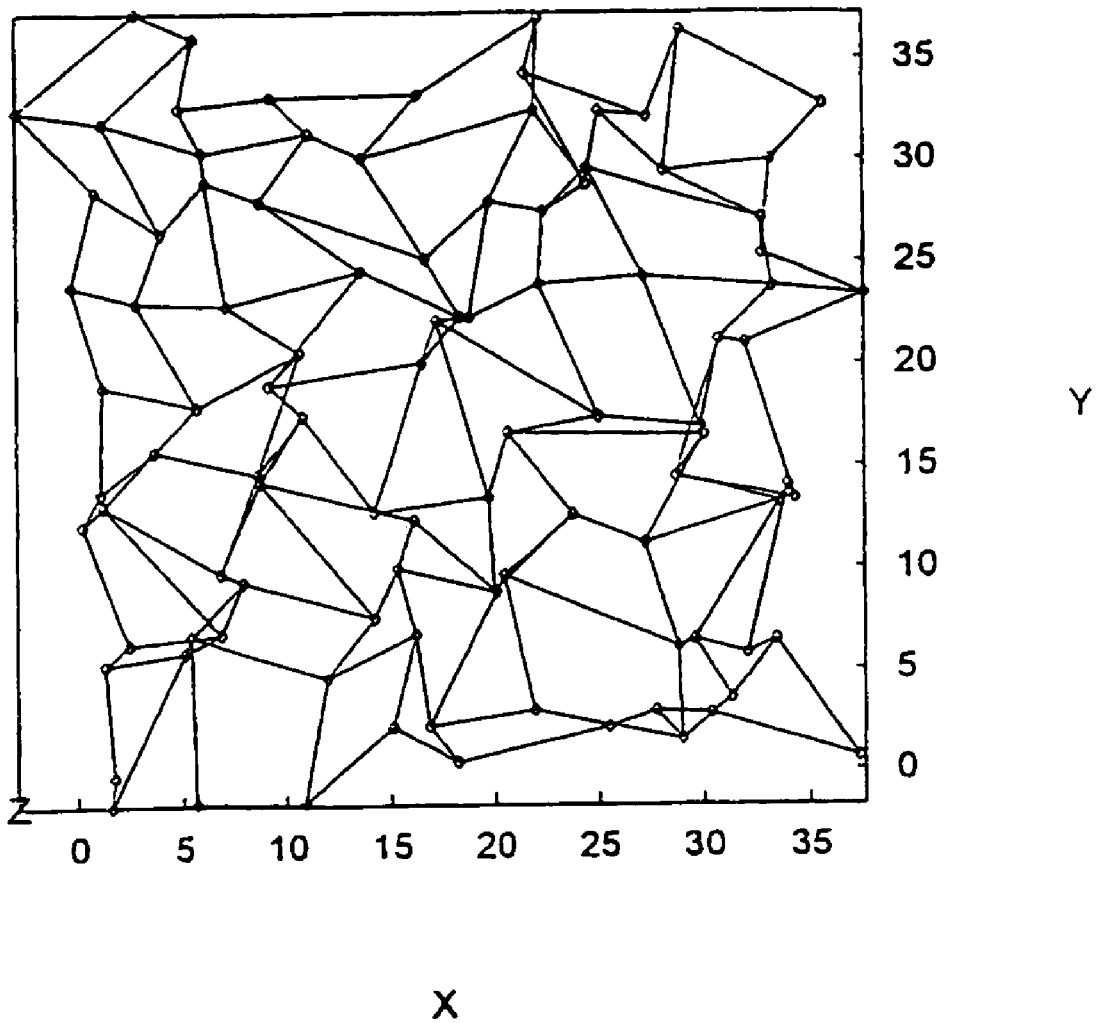
FIG. 7 shows a random arrangement.

Additionally, suppose that the argon atoms are arranged in a more random manner than in the arrangement shown in FIG. 5, for example, the arrangement as shown in FIG. 7. In this case; pairs of very close atoms are generated. Therefore, if a dynamics simulation is performed by using this arrangement as an initial arrangement, a temperature becomes locally high, which leads to an overflow occurrence.

Figure 8:
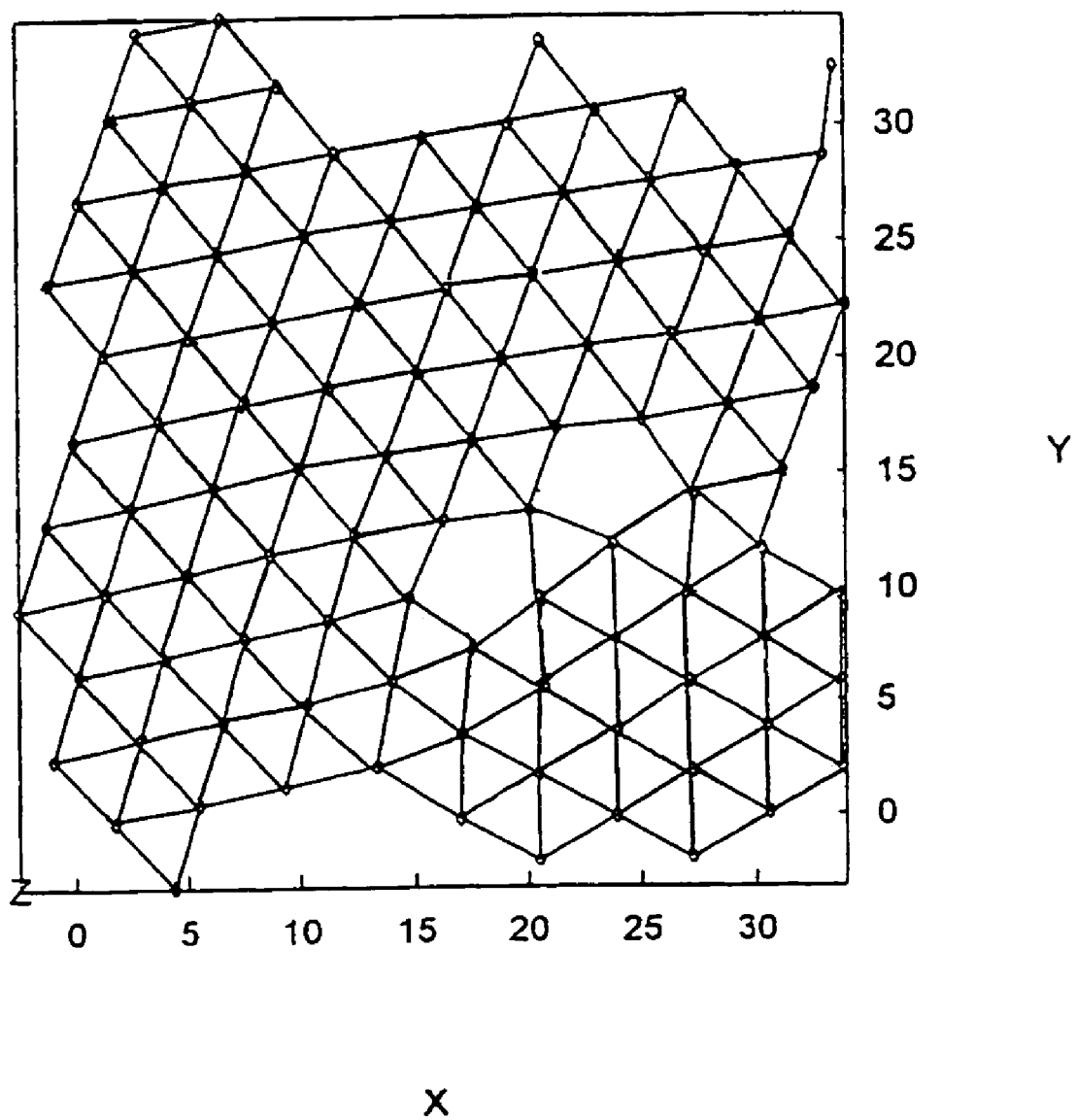
FIG. 8 shows a second equilibrium arrangement.
Figure 9:
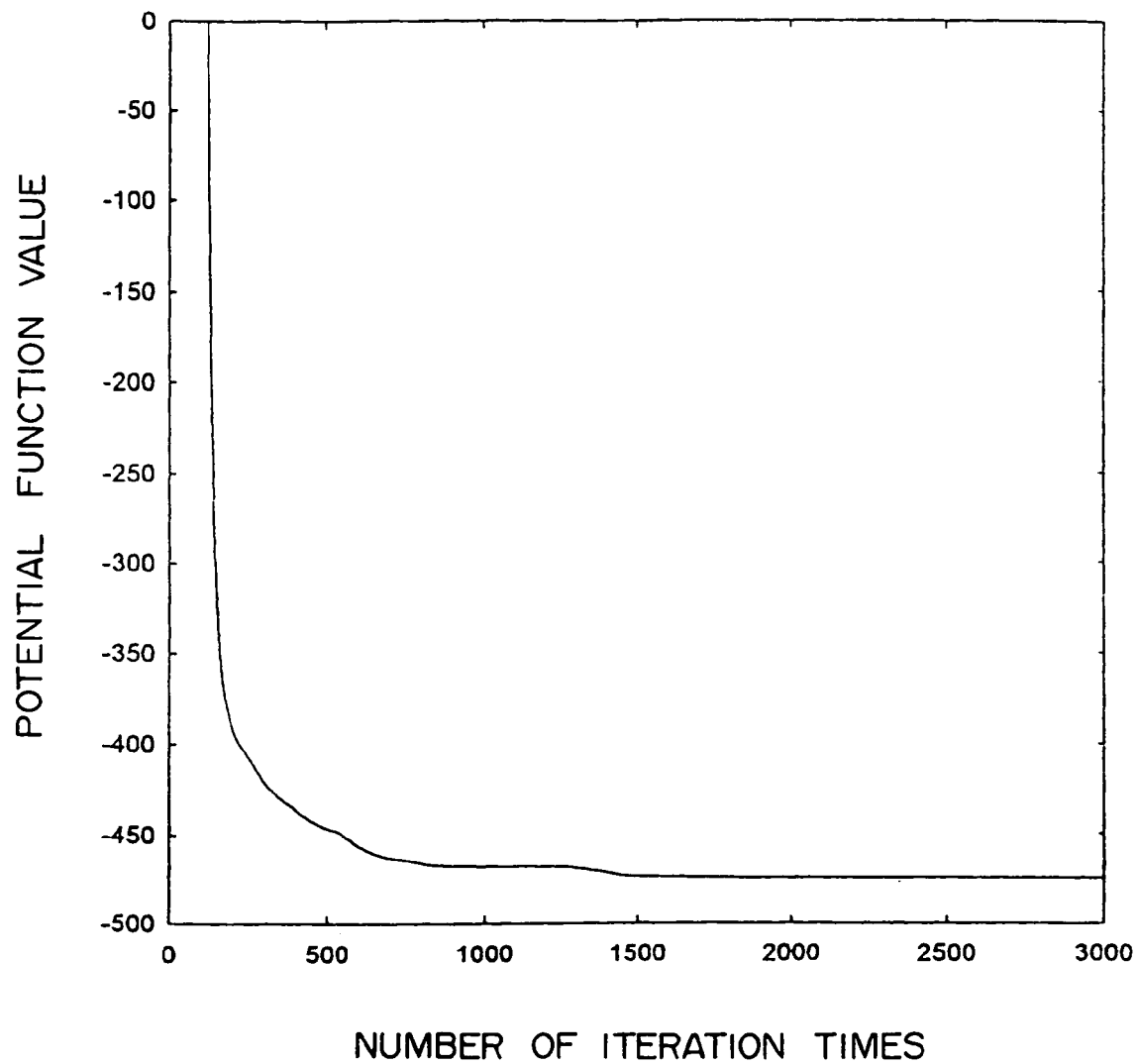
FIG. 9 shows a potential change.

As a result of calculating an equilibrium arrangement with the algorithms shown in FIGS. 4A and 4B starting from this arrangement, the arrangement shown in FIG. 8 is obtained. In FIG. 8, an arrangement analogous to the experimentally acquired structure is obtained in the same manner as in FIG. 6. At this time, the value of the potential function varies as shown in FIG. 9. It is known from FIG. 9 that the value of the potential function monotonically decreases with the iteration of the descent method calculation.

In the above-described preferred embodiments, an equilibrium arrangement is obtained with the relatively simple descent method. Alternatively, a search method such as simulated annealing, or a genetic algorithm may be used. Furthermore, as disclosed by the prior application "Processing Device and Method for Solving an Optimization Problem" (Japanese Patent Application No. 11-16500), an equilibrium arrangement may be obtained by using a search algorithm for determining a low-cost shape while transforming a shape model representing an optimization problem. In this case, particles are used as transformation elements forming the shape model.

Additionally, a set of particles to be simulated is not limited to atoms or molecules. The present invention can be applied to a simulation of an arbitrary set of particles for which an interaction is predefined.

Furthermore, the space where particles are arranged is not limited to a two-dimensional space. The present invention can be applied to a simulation of a set of particles in an arbitrarily dimensional space. Normally, a simulation is performed in a three-dimensional space in many cases.

The above-described generating device can be configured by using an information processing device such as the computer as shown in FIG. 10. The information processing device shown in FIG. 10 comprises a CPU (Central Processing Unit) 21, a memory 22, an input device 23, an output device 24, an external storage device 25, a medium driving device 26, and a network connecting device 27, which are interconnected by a bus 28.

The memory 22 includes, for example, a ROM (Read Only Memory), a RAM (Random Access Memory), and stores the program and data used for processing. The CPU 21 performs necessary processing by executing the program with the memory 22.

The input device 23 is, for example, a keyboard, a pointing device, a touch panel, and is used to input an instruction or information from a user. The output device 24 is, for example, a display, a printer, a speaker, and is used to make an inquiry to a user or to output a process result.

The external storage device 25 is, for example, a magnetic disk device, an optical disk device, a magneto-optical disk device. The information processing device stores the above described program and data onto the external storage device 25, and can use the program and data by loading them into the memory 22, depending on need. Additionally, the external storage device 25 is also used as a database for storing input data files.

The medium driving device 26 drives a portable storage medium 29, and accesses its recorded contents. As the portable storage medium 29, an arbitrary computer-readable storage medium such as a memory card, a floppy disk, a CD-ROM (Compact Disc-Read Only Memory), an optical disk, a magneto-optical disc is used. A user stores the above described program and data in the portable storage medium 29, and can use the program and data by loading them into the memory 22 depending on need.

The network connecting device 27 communicates with an external device via an arbitrary network (line) such as a LAN (Local Area Network), and performs data conversion accompanying a communication. The information processing device receives the above described program and data from the external device via the network connecting device 27, and can use the program and data by loading them into the memory 22 depending on need.

Furthermore, the simulation device simulating a particle system by using an equilibrium arrangement as an initial arrangement includes the above-described generating device, and can be configured by an information processing device similar to that shown in FIG. 10. In this case, CPU 21 performs a simulation process, for MD simulation by executing the program with the memory 22.

Figure 11:
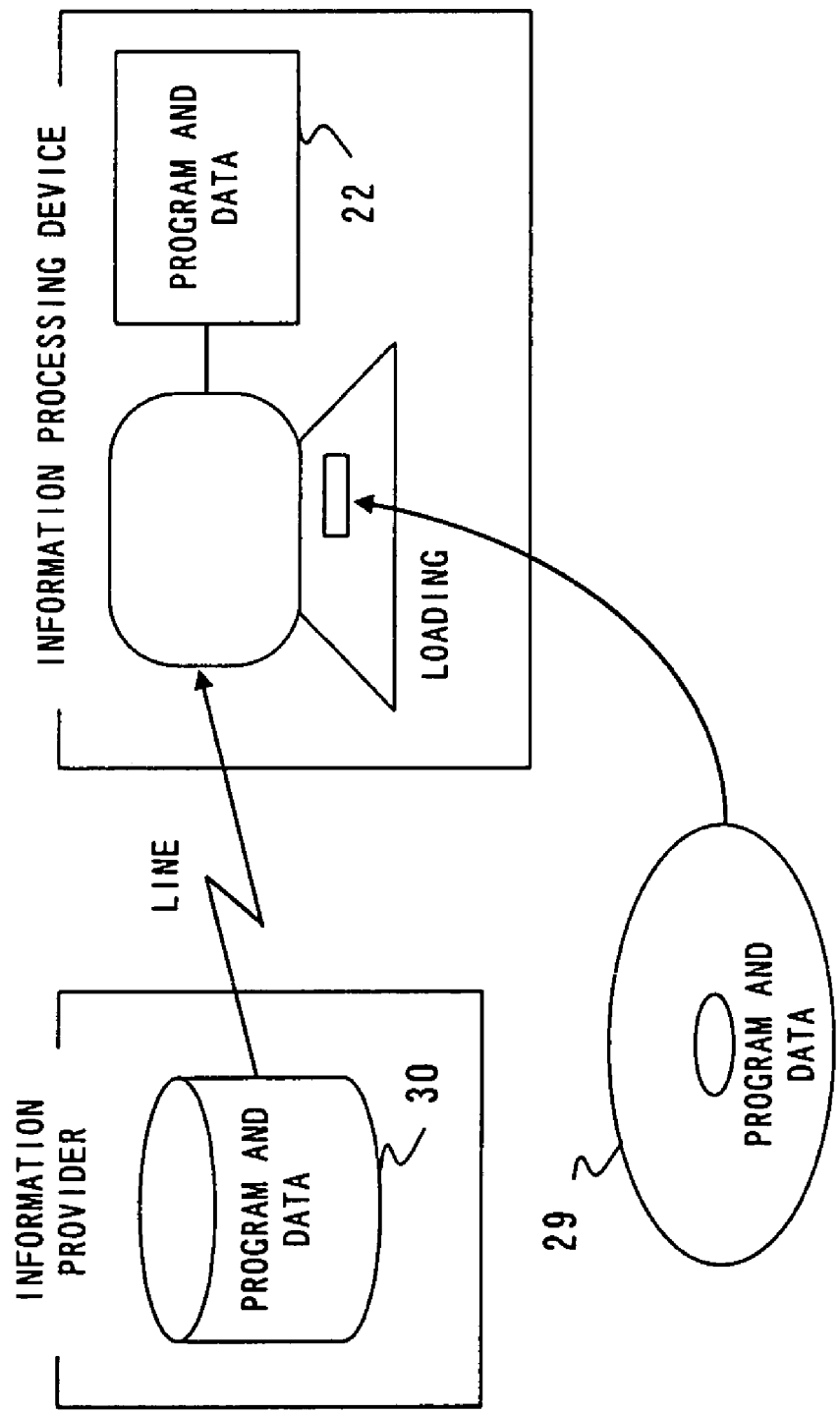
FIG. 11 shows storage media.

FIG. 11 shows computer-readable storage media which can provide a program and data to the information processing device shown in FIG. 10. The program and data stored onto the portable storage medium 29 or in an external database 30 are loaded into the memory 22. The CPU 22 then executes the program by using the data, and performs necessary processing.

According to the present invention, there is no need to consider the velocity of particles as is conventional or to worry about an algorithm failure due to a huge numerical value. Accordingly, it is unnecessary to use the conventional heat emission method, the potential relaxation method or the cell size change method, thereby leading to a reduction in a calculation cost required for these methods and an improvement in simulation operability. Furthermore, various interactions can be handled in a general-purpose manner.

What is claimed is:

1. A generating device for generating an arrangement of a set of particles in a particle system simulation by a computer implemented method, comprising:
    a calculating unit to calculate an equilibrium arrangement of the set of particles in a space; and
    an outputting unit to output an obtained equilibrium arrangement as an initial arrangement used in a simulator to simulate states of molecules formed by the set of particles at various temperatures and pressures,
    wherein said calculating unit calculates the equilibrium arrangement by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in the simulation by the simulator and leads to a failure of a numerical integration algorithm to solve a differential equation in the simulation.

2. The generating device according to claim 1, wherein when the interaction of the particle system is described by a force function, said calculating unit generates the potential function by using the force function.

3. A simulation device using a computer implemented method, comprising:
    a calculating unit to calculate an equilibrium arrangement of a set of particles in a space;
    a simulating unit to perform a particle system simulation by using an obtained equilibrium arrangement as an initial arrangement; and
    an outputting unit to output a result of the simulation to simulate states of molecules formed by the set of particles at various temperatures and pressures,
    wherein said calculating unit calculates the equilibrium arrangement by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in the simulation by the simulating unit and leads to a failure of a numerical integration algorithm to solve a differential equation in the simulation.

4. A generating device for generating an arrangement of a set of particles in a particle system simulation by a computer implemented method, comprising:
  calculating means for calculating an equilibrium arrangement of the set of particles in a space; and
  outputting means for outputting an obtained equilibrium arrangement as an initial arrangement used in a simulator to simulate states of molecules formed by the set of particles at various temperatures and pressures,
  wherein said calculating means calculates the equilibrium arrangement by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in the simulation by the simulator and leads to a failure of a numerical integration algorithm to solve a differential equation in the simulation.

5. A simulation device using a computer implemented method, comprising:
  calculating means for calculating an equilibrium arrangement of the set of particles in a space;
  simulating means for performing a particle system simulation by using an obtained equilibrium arrangement as an initial arrangement; and
  outputting means for outputting a result of the simulation to simulate states of molecules formed by the set of particles at various temperatures and pressures,
  wherein said calculating means calculates the equilibrium arrangement by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in the simulation by the simulating means and leads to a failure of a numerical integration algorithm to solve a differential equation in the simulation.

6. A computer-readable storage medium on which is recorded a program for causing a computer to execute a process for generating an arrangement of a set of particles in a particle system simulation, said process comprising:
  calculating an equilibrium arrangement of the set of particles in a space by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in the simulation by a simulator and leads to a failure of a numerical integration algorithm to solve a differential equation in the simulation; and
  outputting an obtained equilibrium arrangement as an initial arrangement used in the simulator to simulate states of molecules formed by the set of particles at various temperatures and pressures.

7. A computer implemented simulation method, comprising:
  calculating an equilibrium arrangement of a set of particles in a space by repeating a calculation of a value of a potential function, which represents an interaction of the particle system, and is described by positions of the set of particles in the space, while displacing each component of a positional vector of each of the particles in positive and negative directions by only a specified amount, and by comparing values of the potential function after positive and negative displacement with a value of the potential function before the displacement to obtain a new position of each of the particles, the obtained new position avoiding a generation of a pair of close particles which causes a high temperature in a neighborhood of the pair in a particle system simulation and leads to a failure of a numerical integration algorithm to solve a differential equation in the simulation; and
  performing the particle system simulation to simulate states of molecules formed by the set of particles at various temperatures and pressures by using an obtained equilibrium arrangement as an initial arrangement.

8. The computer implemented simulation method according to claim 7, further comprising:
  establishing a convergence condition, when a difference between successive calculations of the potential function of the set of the particles is below a predetermined level; and
  terminating said calculating, when said established convergence condition exists.

9. A generating device for generating an arrangement of a set of particles in a particle system simulation, comprising:
  a calculating unit to calculate an equilibrium arrangement of N particles in a m-dimensional space by displacing a component $q_i$ of a positional vector of each of the N particles (i=1, . . . , n, n=Nm) in positive and negative directions by only a specified amount to obtain qi+ and qi−, respectively, calculating values of a potential function $U(q_1, \ldots, q_n)$ with $q_i$=qi+ and qi=qi− to obtain U(i)+ and U(i)−, respectively, comparing U(i)+ and U(i)− with a value of $U(q_1, \ldots, q_n)$ before a displacement, and adopting one of the qi+, the qi−, and a current value of $q_i$, as a new value of $q_i$ according to a comparison result, the new value avoiding a generation of a pair of close particles which causes a high temperature in a neighborhood of the pair in the simulation by a simulator and leads to a failure of a numerical integration algorithm to solve a differential equation in the simulation; and
  an outputting unit to output an obtained equilibrium arrangement as an initial arrangement used in the simulator to simulate states of molecules formed by the set of particles at various temperatures and pressures.

10. A generating device for generating an arrangement of a set of particles in a particle system simulation by a computer implemented method, comprising:

a calculating unit to calculate an equilibrium arrangement of the set of particles in a space; and an outputting unit to output an obtained equilibrium arrangement as an initial arrangement used in a simulator to simulate states of molecules formed by the set of particles at various temperatures and pressures, wherein said calculating unit calculates the equilibrium arrangement by repeating a calculation of a value of a potential function, which represents an interaction of the particle system, and is described by positions of the set of particles in the space, while displacing each component of a positional vector of each of the particles in positive and negative directions by only a specified amount, which does not continually change and does not lead to a failure of a numerical integration of a Newtonian equation, and by comparing values of the potential function after positive and negative displacement with a value of the potential function before the displacement to obtain a new position of each of the particles.

11. A generating device for generating an initial arrangement of a set of particles usable by a particle system simulation solvable by a differential equation, comprising:

a calculating unit which calculates an equilibrium arrangement of the set of particles in a space by repeating a calculation of a value of a potential function while micro-displacing each component of a positional vector of at least one particle to obtain a new position of the at least one particle by comparing values of the potential after the micro-displacement with values before the micro-displacement; and an outputting unit which outputs the equilibrium arrangement as an initial arrangement used in a particle simulation, wherein the new position avoids a generation of a pair of close particles which causes a local high temperature which leads to a failure of a numerical integration algorithm which solves the differential equation.

12. The generating device of claim 11, wherein, when the interactions of particles in the particle system are described by a force function, the calculating unit generates the potential function by using the force function.

13. The generating device of claim 11, wherein the particle system simulation is implementable by a computer.

14. The generating device of claim 11, wherein the particle system simulation simulates states of molecules formed by the set of particles at various temperatures and pressures.

15. The generating device of claim 11, wherein the potential function represents an interaction of each particle in the particle system and is described by positions of the particles in the space.

16. The generating device of claim 11, wherein the component of the positional vector is displaced only a specified amount.

17. The generating device of claim 11, wherein the component of the positional vector is displaced in a positive and a negative direction.

18. The generating device of claim 11, wherein each of the particles in the set of particles is displaced.

* * * * *

UNITED STATES PATENT AND TRADEMARK OFFICE
CERTIFICATE OF CORRECTION

| | |
|---|---|
| PATENT NO. | : 7,065,477 B2 |
| APPLICATION NO. | : 09/435215 |
| DATED | : June 20, 2006 |
| INVENTOR(S) | : Ikuo Fukuda et al. |

It is certified that error appears in the above-identified patent and that said Letters Patent is hereby corrected as shown below:

Column 12, Line 53, after "and" change "qi=qi-" to --$q_i$=qi---.

Signed and Sealed this

Seventh Day of November, 2006

JON W. DUDAS
*Director of the United States Patent and Trademark Office*